United States Patent [19]
Mandanis

[11] Patent Number: 5,152,352
[45] Date of Patent: Oct. 6, 1992

[54] PNEUMATIC PERCUSSION TOOL, ESPECIALLY FOR THE PREPARATION OF BONES

[75] Inventor: Georges Mandanis, Luzern, Switzerland

[73] Assignee: IMT Integral Medizintechnik AG, Ennetburgen, Switzerland

[21] Appl. No.: 612,887

[22] Filed: Nov. 13, 1990

[30] Foreign Application Priority Data

Apr. 20, 1990 [CH] Switzerland ............... 1345/90

[51] Int. Cl.⁵ ................................................ B25D 17/06
[52] U.S. Cl. ......................................... 173/17; 173/91;
                                            173/135; 173/211; 91/234
[58] Field of Search ............... 173/17, 91, 135, 136,
                                            173/139, 137; 91/234

[56] References Cited

U.S. PATENT DOCUMENTS

| | | | |
|---|---|---|---|
| 1,264,318 | 4/1918 | McGrath | 173/136 |
| 1,440,731 | 1/1923 | Gartin | 173/135 |
| 2,426,409 | 8/1947 | O'Farrell | 173/135 |
| 2,440,457 | 4/1948 | Beckwith | 173/135 |
| 3,583,499 | 6/1971 | Cordes | 173/91 |
| 4,114,950 | 9/1978 | Cooper | 173/91 |
| 4,651,833 | 3/1987 | Karpf et al. | 173/136 |

*Primary Examiner*—Frank T. Yost
*Assistant Examiner*—Scott A. Smith
*Attorney, Agent, or Firm*—Fish & Richardson

[57] ABSTRACT

A piston is oscillating periodically within a cylinder, propelled by compressed air. At at least one of its end positions, the piston generates a stroke that acts on a working tool, e.g. a rasp. The sizes of the piston surfaces acted upon by the compressed air and the capacities at the cylinder volumes limited by the piston are dimensioned such that the impact momentum of the piston at both end positions is essentially the same. In case of a bone rasp working tool this equal momentum of the stroke advancing the rasp into the bone and the stroke loosening the tool by retracting it, leads to an optimum working of the bone and as little stress as possible on the patient.

6 Claims, 8 Drawing Sheets

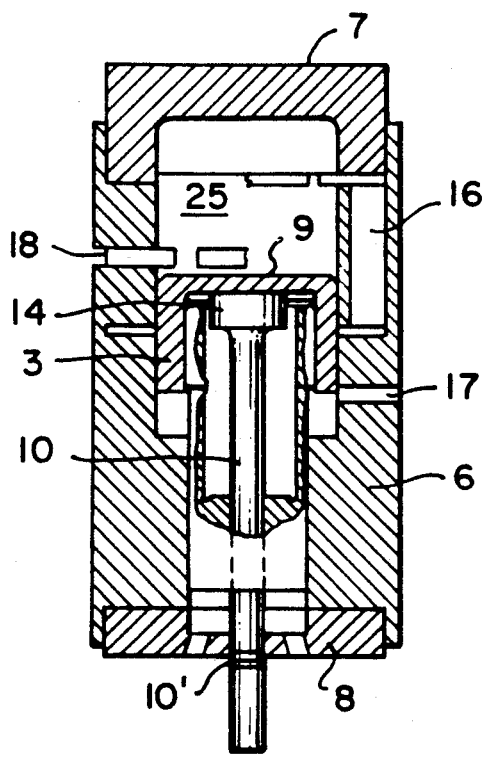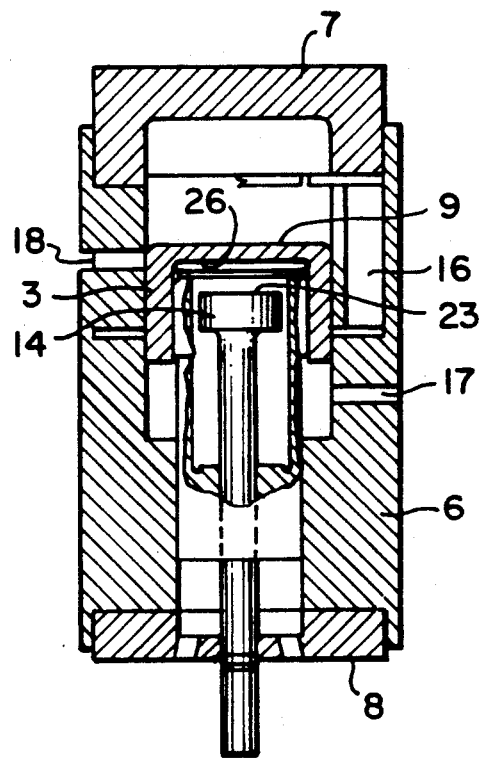
FIG. 4a  FIG. 4b
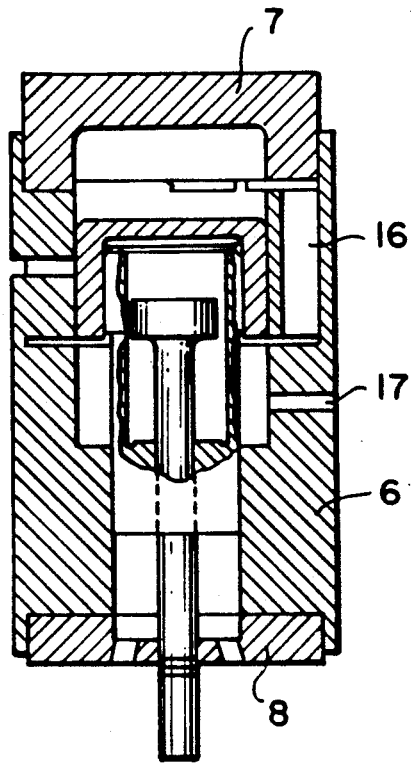
FIG. 4c

PNEUMATIC PERCUSSION TOOL, ESPECIALLY FOR THE PREPARATION OF BONES

BACKGROUND OF THE INVENTION

1. Field of the Invention

The invention relates to a pneumatic percussion tool comprising a cylinder, a socket for a working tool and a piston arranged displaceable in said cylinder and acting as an oscillating striking member, said piston being provided with a first surface to be acted upon by compressed air for propelling said piston in forward direction towards said working tool, a second surface, facing away from said first surface, to be acted upon by compressed air for propelling said piston backward, and with two striking surfaces, by which a strike on said tool can be effected at both dead centers of said piston oscillations, each to generate a pulse advancing said working tool into a workpiece or retracting and loosening said working tool from said workpiece, respectively, said percussion tool comprising at least one transfer port between said first and said second surface, said port being controlled by said piston, and at least one air outlet, said port and said outlet controlling the compressed air distribution for the piston forward and backward movement.

2. Description of the Prior Art

A penumatic oscillating tool or percussion tool, respectively, for bone preparing tools, especially for rasps for the working of the bearing surfaces of bones that shall receive an artificial joint member, is is known from the Swiss Patent No. 661 239 (corresponding to U.S. Pat. No. 4,651,833). It has been found, however, that despite the loosening action exerted on the working port of the tool, an optimum action of such a tool is not attained, since the rearward momentum is too low to securely retract the tool from the cavity.

SUMMARY OF THE INVENTION

Hence, it is a general object of the present invention to provide a pneumatic percussion tool that allows the fast and easy and most careful removing of bone material from the bone and working of the bearing surfaces for the artificial joint member.

It is a further object of the invention to provide an impact tool for general purposes (e.g. for the building industry) that generates an effective rearward momentum of the tool, allowing an easy retraction of the tool.

Now, in order to implement these and still further objects of the invention, which will become more readily apparent as the description proceeds, the pneumatic percussion tool or impact tool, respectively, is manifested by the features that the size of said first surface, the size of said second surface and the volumina of the cylinder volume defined by said cylinder and said first piston surface and the transfer port volume are selected such that at a predetermined piston position, and a predetermined compressed air pressure value, the impact momentum of the forward moving piston is substantially equal to the impact momentum of the backward moving piston.

In a preferred embodiment a force receiving member or rod, respectively, is arranged within the cylinder. By this member, the impact momentum of the piston can be transmitted directly to the working tool. This allows a construction of the cylinder from materials that are light and inexpensive, e.g. the cylinder can be made of plastics or aluminium.

Several embodiments are possible. The forward impact (in working tool direction) may result from the impact of the piston on the front cylinder cover at the end of the forward piston path, and the backward impact may result from the impact of the backward propelled piston on the force receiving member. On the contrary, the forward impact may act on the member and the backward impact on the other cylinder cover facing away from the working tool. In the preferred embodiment, however, the forward impact and the backward impact of the piston act both on the member. In this case, even both cylinder covers may be made of plastics or aluminium.

In a further preferred embodiment, the longitudinal position of the force receiving member or rod, respectively, is adjustable within the cylinder. This allows a selection of different operation modes of the tool. Accordingly, depending on the adjustment position, the same tool may selectively generate only forward impacts, or only rearward impacts; or even an idle position can be selected.

BRIEF DESCRIPTION OF THE DRAWINGS

The invention will better understood and objects other than those set forth above will become apparent when consideration is given to the following detailed description thereof. Such description makes reference to the annexed drawings, wherein:

FIGS. 4a to 4e are views of different piston positions during forward impact operation of yet another embodiment;

DESCRIPTION OF THE PREFERRED EMBODIMENTS

Figure 1:
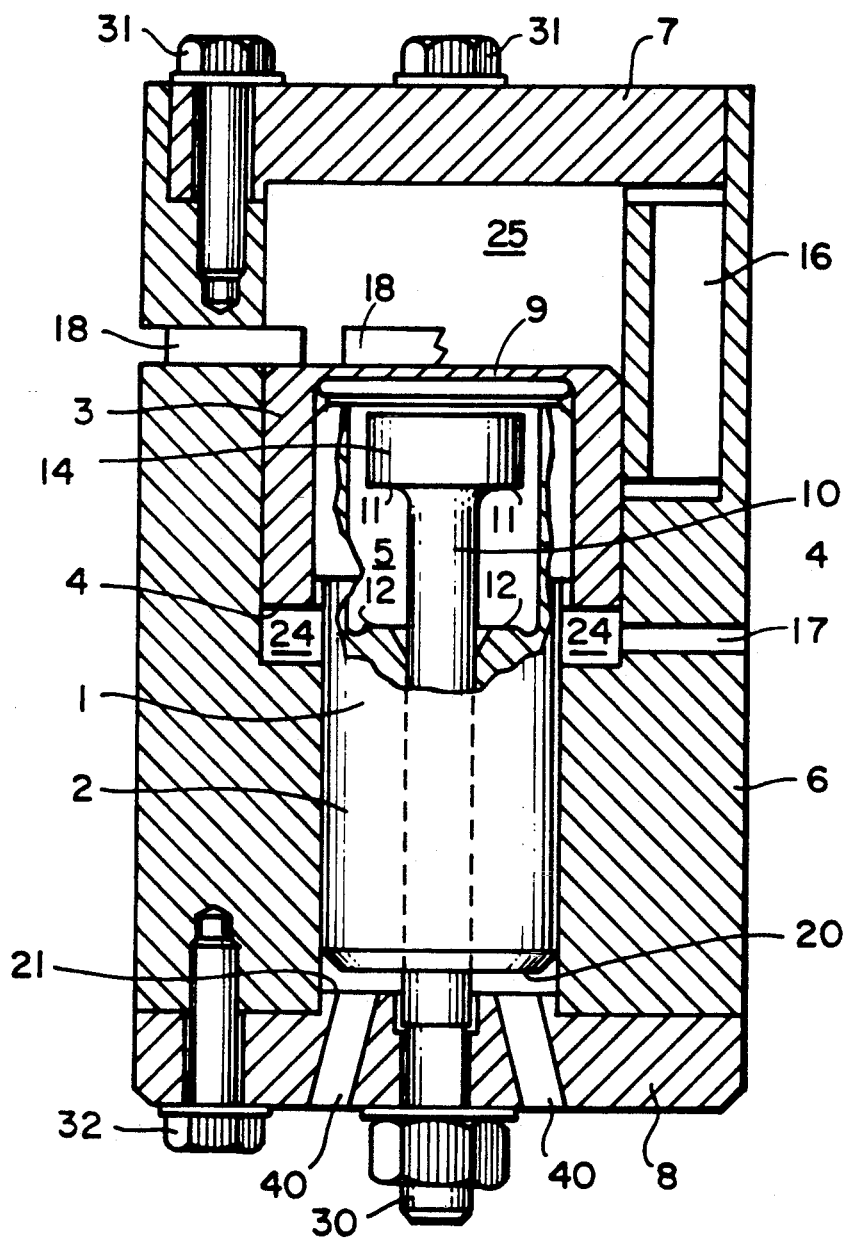
FIG. 1 is a partly sectional view of a first embodiment of the impact tool.

A first embodiment is now described with reference to FIG. 1. A piston 1 is displaceably arranged within a cylinder 6. The cylinder is closed by an upper cover 7, and by a lower cover 8 provided with outlets 40. The covers 7, 8 are attached to the cylinder body by means of threaded bolts 31 and 33, respectively. The piston 1 is a stepped piston having an upper piston section 3 provided with a larger diameter than the lower piston section 2. The annular piston area formed by the step is designated by reference numeral 4. The cylinder 6 has two sections as well with different inner diameters, according to the shape of the stepped piston. A rod 10 having the function of a force receiving member is mounted on the lower cover 8 and extends into the cylinder and the piston. A socket (not shown) for holding a working tool, e.g. a bone rasp or a hammer for construction work, is arranged at the end 30 of the rod 10 extending outwardly from the cylinder. The other end of the rod 10 is arranged within the cylinder and the piston, respectively, and is provided with an expanded head 14. This head 14 is provided with at least a first impact surface 11 for the piston 1. The piston is provided accordingly with a bore for the shaft of the rod and with a recess 5 of larger diameter than the bore, in which recess the head 14 of the rod is situated. Where the bore of the piston passes over to the recess 5 of the piston, the piston is provided with a striking surface 12, which — as will be described later — is adapted to act upon the impact surface 11.

In the shown embodiment there is provided a second impact surface 21 on the inside of the lower cylinder cover 8 and, accordingly, a second striking surface 20 on the outside of the lower piston end.

The upper piston section 3 divides the wider cylinder area into two cylinder volumes 24 and 25, respectively, which are limited by the piston area 4 and 9, respectively. The area 4 is annular shaped and has a smaller surface size than the area 9. The cylinder volumes 24 and 25, respectively, have a variable capacity or volume, respectively, depending from the position of the piston within the cylinder. The two volumina 24, 25 are connected with each other by at least one transfer port 16 arranged in the cylinder wall, and the inlet of this port is opened and closed by the piston section 3; in other words, the position of the piston decides whether the cylinder volumes 24 and 25 are interconnected or not. Further, a compressed air inlet 17 opens into the lower cylinder volume 24, for feeding compressed air from a compressed air source (not shown) into the lower cylinder volume 24. At least one outlet 18 is provided in the upper cylinder volume and is opened and closed by the piston section 3 as well.

Figure 2A:
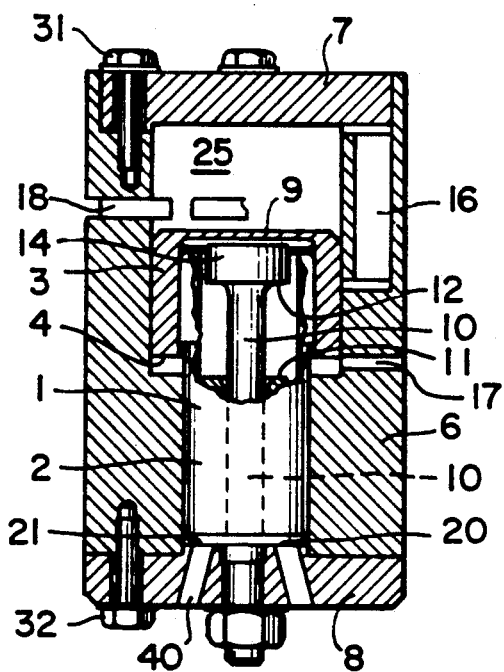
FIGS. 2a to 2d are views of different positions of the piston during operation of the tool according to FIG. 1.
Figure 2B:
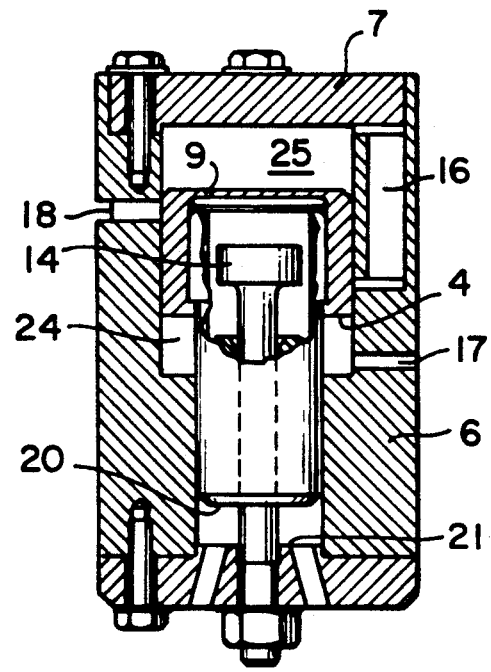
Figure 2C:
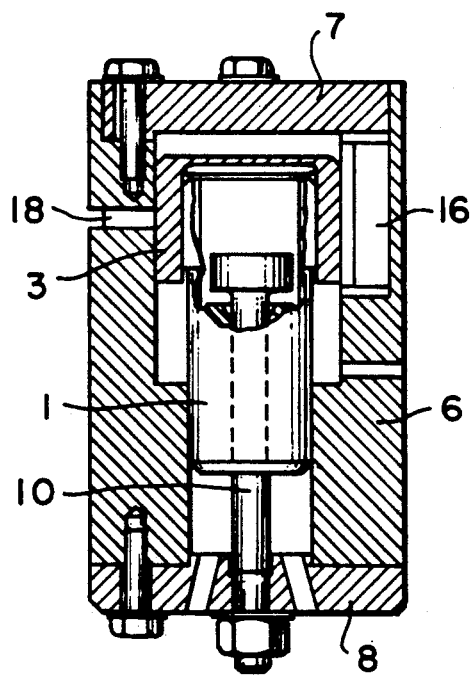
Figure 2D:
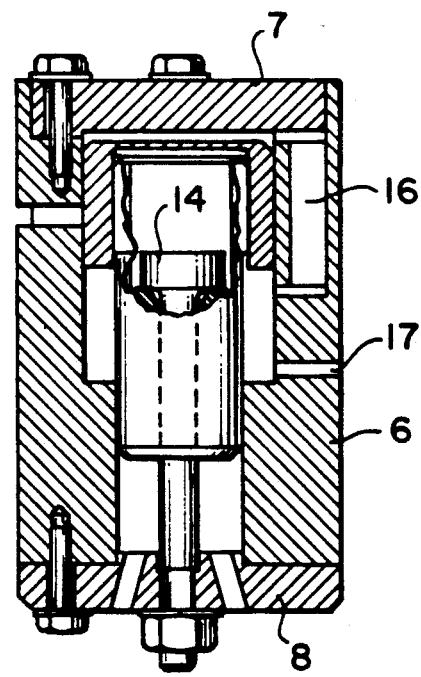

Referring now to FIGS. 2a to 2d the operation of the percussion tool will be explained. FIG. 2a shows the piston 1 at its bottom dead center, where the piston impacts with its striking surface 20 on the impact surface 21 of the cylinder cover 8, and thus generates a forward driving impact pulse for the working tool, e.g. the bone rasp (not shown). By the compressed air inlet 17, compressed air with a pressure of preferably approximately 7 bar enters the lower cylinder volume 24 and acts on the piston 1 via the annular surface 4. Since the outlet 18 in the upper cylinder volume 25 is opened, the normal ambient pressure of about 1 bar is present in the volume 25. This difference between the pressures within the volumina 24, 25 of the cylinder causes a backward (or upward with respect to the drawings) directed acceleration of the piston. During the upward displacement of the piston 1, the outlets 18 will be closed (FIG. 2b). Accordingly, the air trapped within the upper volume 25, which volume gets smaller, will be compressed. FIG. 2c shows the position of the piston 1 at which the transfer port 16 is opened. By this transfer port 16 the upper cylinder volume 25 is then connected with the compressed air source as well and the pressure in volume 25 is now approximately 7 bar as well. Caused by its momentum, the piston 1 moves still upward but is now decelerating, since the pressure of 7 bar now acts on the upper piston surface 9 as well, which is larger than the annular piston surface 4, and thus a forward (or downward with respect to the drawings) directed force is exerted on the piston 1. FIG. 2d shows the piston 1 reaching its top dead center, at which position the still decelerating piston 1 impacts on the force receiving member 10 with the remaining velocity of its upward movement. Upon collision, the striking surface 12 of the piston 1 impacts on the impact surface 11 of the head 14 of the rod 10. From the impact a force results that drives the tool backwards, retracting and loosening any working tool driven by the percussive tool. After the impact the piston accelerates downward because of the 7 bar pressure on the surface 9. During the downward movement of the piston 1, the transfer port 16 is closed and at first, expansion of the air in the upper cylinder volume occurs and afterwards, the air will be flowing out through the opening outlet 18. The piston 1 moves further downward because of its momentum and against the breaking force caused from the compressed air acting on the surface 4, until it reaches again the bottom dead center where it collides with the remaining velocity on the cylinder cover 8 (FIG. 2a).

For attaining a ratio of about 1 between the pulse on the tool in forward direction and the pulse in backward direction, the dimensioning of the percussion tool should follow the rules below, where a first parameter A is defined as follows:

$$A = \frac{A_1}{A_2} \cdot \frac{P_0}{P_2}$$

wherein $A_1$ is the size of the upper surface 9 of the piston
$A_2$ is the size of the annular surface 4 of the piston
$P_0$ is the ambient pressure (approx. 1 bar)
$P_2$ is the pressure of the compressed air source (approx. 7 bar)

(1 bar equals 100'000 Pascal).

Two additional parameters are defined as follows:

$$V_u = \frac{V_{12}}{V_A} \text{ and } V_o = \frac{V_T}{V_A};$$

wherein $V_A$ is the volume of the transfer port 16 plus the volume of the upper cylinder volume 25 at the piston position where the outlet 18 is being closed by the piston (FIG. 2b);

$V_{12}$ is the volume of the transfer port 16 plus the volume of the upper cylinder volume 25 at the piston position where the transfer port 16 is being opened (FIG. 2c) and $V_T$ is the volume of the transfer port plus the volume of the upper cylinder volume 25 at the top dead center of the piston (FIG. 2d).

The desired ratio of 1 of the impact pulses is attained when the parameters meet substantially the following conditions:

$$0.1 \leq A \leq 0.5 \quad \text{(I)}$$

and $$0 \leq V_o \leq V_u \leq 1 \quad \text{(II)}$$

Preferably the parameters $V_o$, $V_u$ are in the range of 0.1 to 0.8.

Figure 3:
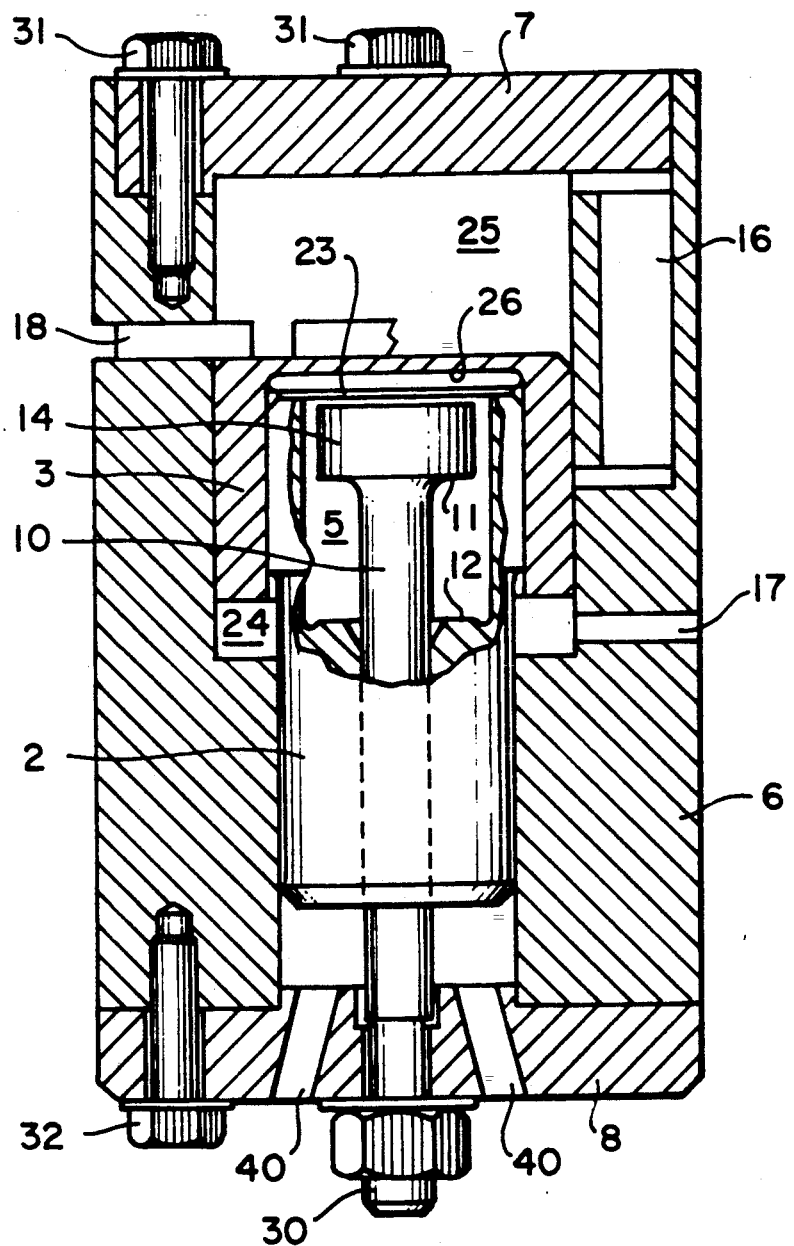
FIG. 3 is a partly sectional view of another embodiment of the tool.

FIG. 3 shows another embodiment, wherein the same parts are depicted with the same reference numerals as in the embodiment above. The difference to the above embodiment is that the lower section 2 of the piston 1 is shorter, and thus the collision of the piston during forward (downward) motion does not occur on the cylinder cover 8 but, as during backward motion, on the head 14 of the force receiving member 10. Therefore, the head 14 is provided with a second impact surface 23 and the inner surface of the top of the piston provides the second striking surface 26. The advantage of this embodiment is that the striking forces act on the force receiving member 10 only, which is directly connected to the working tool (e.g. the bone rasp). Thus the cylinder itself, including the cylinder covers 7 and 8, does not have to endure high stresses due to the striking forces and can be made of less expensive and lighter materials, e.g. of aluminium or plastics, instead of steel.

FIGS. 4a to 4e, 5a to 5d and 6a to 6d show different modes of operation of yet another embodiment of the invention. In this embodiment the tool can be adjusted such that collisions between piston and cylinder occur selectively in forward direction of the piston only, or in backward direction only; or that no strokes occur at all (idle operation). This selection is attained by the feature that the force receiving member 10 can be adjusted and fixed in several different positions along the longitudinal axis of the cylinder. FIGS. 4a to 4e show the operation of the tool for effecting a stroke in forward direction that would advance a bone rasp into the bone or would advance a working tool into a wall. The same reference numerals are used for the same parts as in the already described embodiments. A mark 10' is shown on the rod 10 for a better marking of the different positions of the rod in FIGS. 4, 5 and 6.

With reference to FIG. 4a the piston 1 is shown at its bottom dead center where the striking surface 26 of the piston hits the impact surface 23 of the head 14 and generates a blow acting on the tool that drives the working tool forward. By the pressure of 7 bar on the annular surface 4 the piston 1 is propelled from its bottom dead center in direction of the cylinder cover 7. On its way the piston closes the outlet 18 (FIGS. 4, 6) and compression occurs within the cylinder volume 25. When the piston position of FIG. 4c is reached, the transfer port 16 is being opened and compressed air is let into the upper cylinder volume 25. The upward moving piston 1 is braked by the force exerted on the surface 9.

Figure 4D:
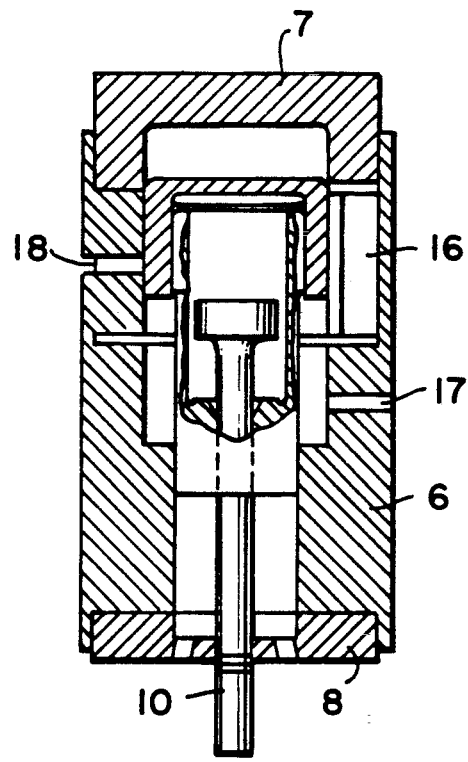
Figure 4E:
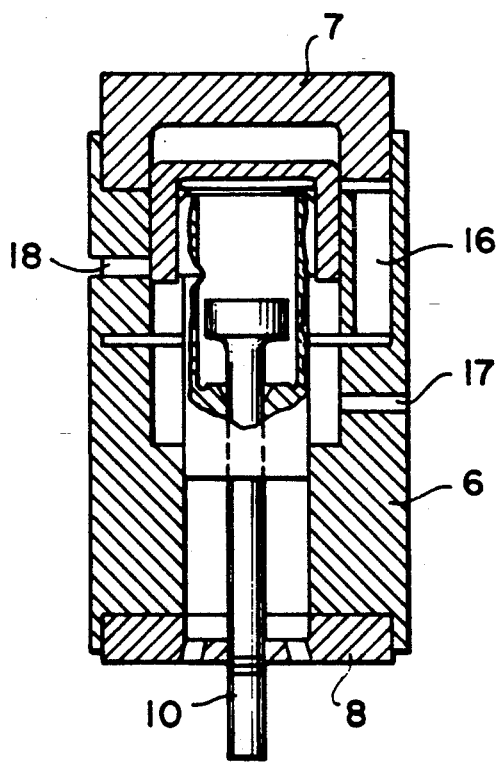

In FIG. 4d the transfer port 16 is closed by the upper piston edge. An air volume (brake volume) is trapped in the cover 7 of this embodiment which exerts a rapidly rising braking force on the piston moving upwards. FIG. 4e shows the top dead center of the piston 1, which is reached by gently braking the piston movement by the brake volume, and without the piston colliding with the cylinder and impacting on the strike surface 11 with its impact surface 12. The rearward movement of the piston is thus ended without a stroke on the tool. By the expansion of the brake volume the piston is again accelerated downward (in forward direction) and the transfer port 16 is opened by the upper piston edge and the pressure of 7 bar acts on the surface 9, further accelerating the piston 1. Expansion occurs in the upper cylinder volume 25 after closing of the transfer port 16 by the lower piston edge and afterwards, the outlet will be opened. Despite a braking of the piston 1 by the pressure on the annular surface 4, the bottom dead center results from the impact of the piston on the surface 23 (FIG. 4a). Thus, a stroke occurs only at the bottom dead center, whereas a gentle, strikeless braking occurs at the top dead center.

FIGS. 5a to 5d show the reverse operation: a stroke at the top dead center and therefore a back-ward, tool retracting motion of the bone rasp or any other working tool, and a gentle strikeless braking of the piston at the bottom dead center. To attain this operation mode the rod 10 is displaced along the longitudinal cylinder axis relative to the cylinder. This displacement can be best noted by comparing the pistion of the mark 10' relative to the cover 8 in FIG. 4 and FIG. 5.

Figure 5A:
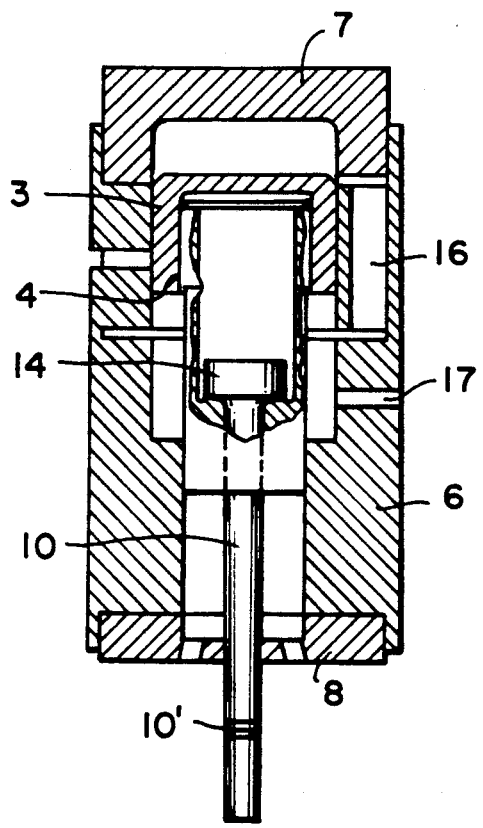
FIGS. 5a to 5d are views of piston positions of the embodiment of FIGS. 4 during backward operation.
Figure 5B:
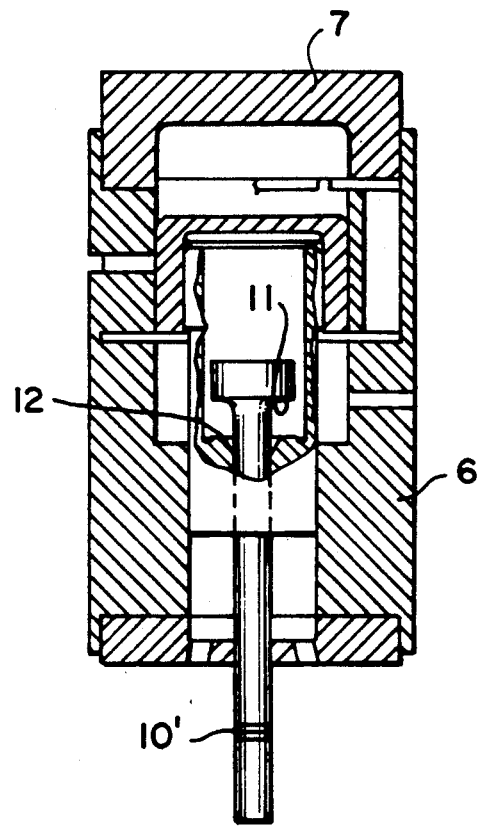

FIG. 5a shows the piston at top dead center position, at which position the stroke occurs by the impact of the piston on the impact surface 11 of the head 14. Afterwards, the piston is accelerated downward in direction of the cover 8 by the pressure of 7 bar acting on the surface 9 and on the smaller, annular surface 4 (FIGS. 5 and 6).

Figure 5C:
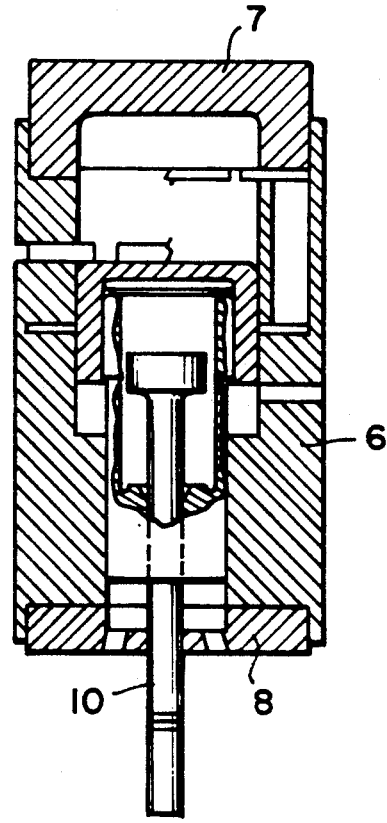
Figure 5D:
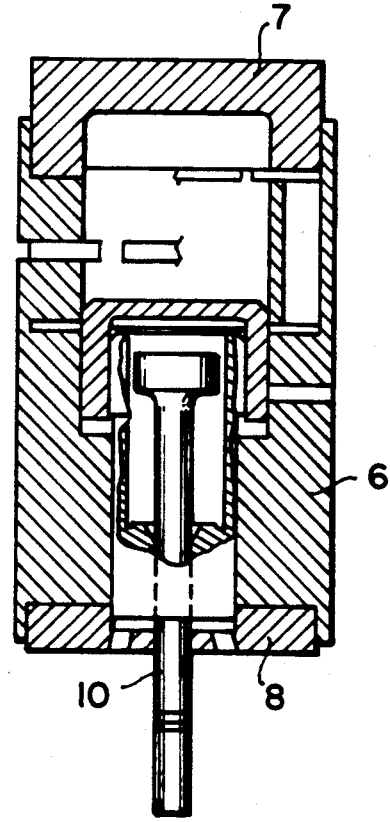

FIG. 5c shows the braking of the piston when the 7 bar pressure acts on the annular surface 4 and approximately 1 bar ambient pressure acts, with open outlet 18, on the surface 9. By means of the brake volume in the volume 24 and a closed inlet 17, a gentle braking of the piston at the bottom dead center occurs in this mode (FIG. 5d), without an impact of the piston on the impact surface 23 causing a stroke, since the rod 10 is displaced compared to the position of the rod in FIGS. 4. The expansion of the brake volume propels the piston upward again and the compressed air inlet 17 is opened, which causes an acceleration of the piston in upward direction.

Figure 6A:
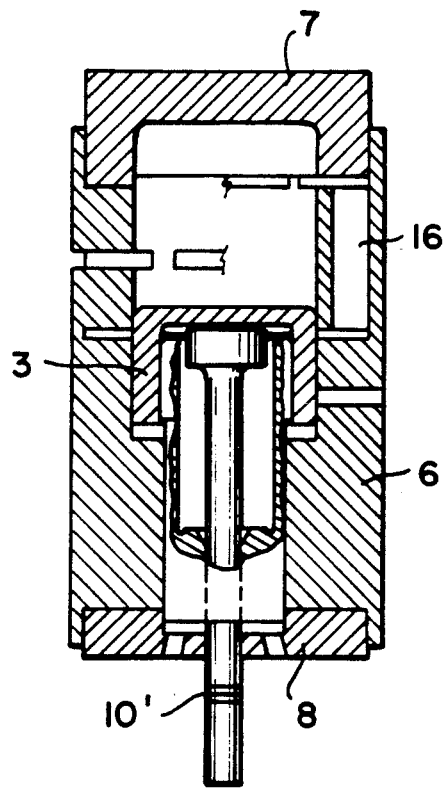
FIGS. 6a to 6d are views of the embodiment of FIGS. 4 and 5 during idle operation.
Figure 6B:
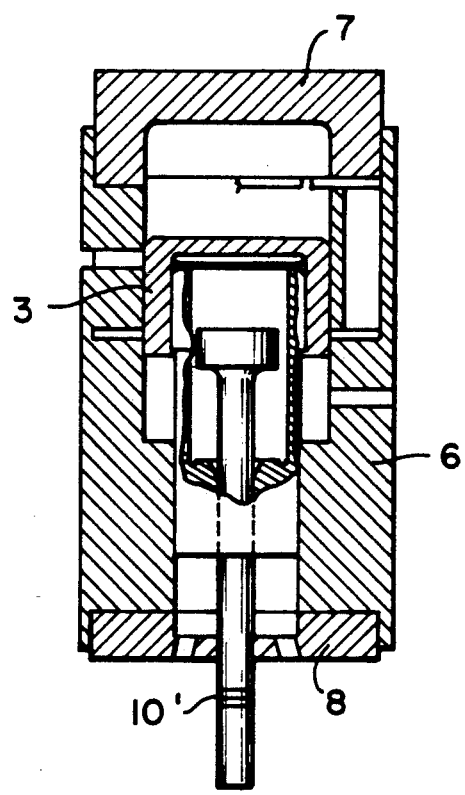
Figure 6C:
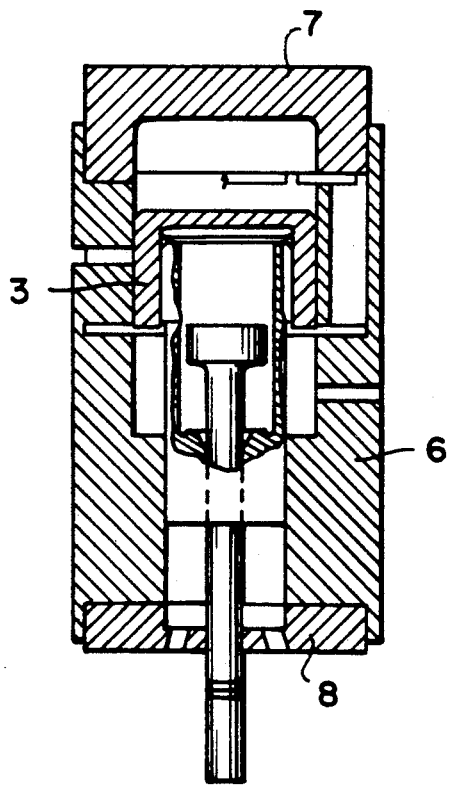
Figure 6D:
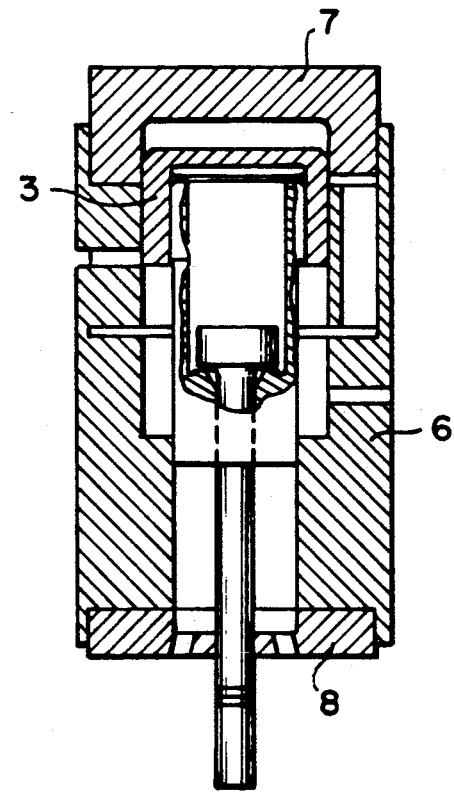

FIGS. 6a to 6d show the idle operation mode. The rod 10 is displaced relative to the cylinder into a position that lies between the positions of FIGS. 4 and 5. A gentle braking with the respective braking volume occurs in this position at the top dead center as well as at the bottom dead center of the piston. That means, that in both end positions of the piston, there is no impact on the rod 10. The percussion tool does operate, but it does not produce any blows on the working tool. FIG. 6a shows the braked piston at the bottom dead center without contact with the impact surface 23. FIG. 6b shows the accelerated upward movement of the piston caused by pressure exertion on the annular surface 4. FIG. 6c shows the opening of the transfer port 16 and FIG. 6d shows the piston at the top dead center without contact with the impact surface 11. The adjustment of the rod relative to the cylinder 6 can be effected by an outside screw thread provided on the rod 10 and a respective thread provided at the bore in the cover 8 holding the rod. By rotating the rod, a displacement in the longitudinal cylinder axis is achieved. The three operation modes can be marked by visible marks on the rod.

Figure 7:
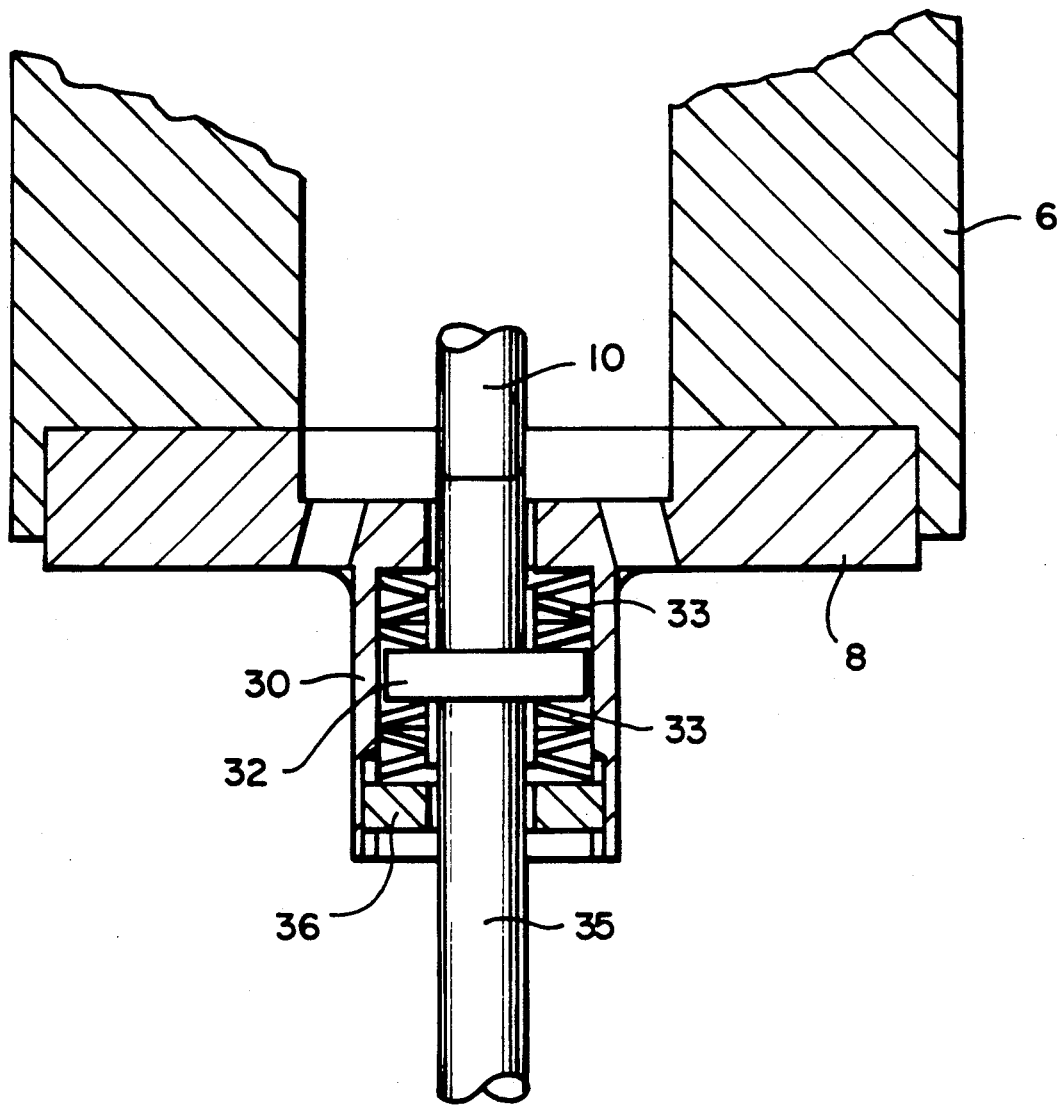
FIG. 7 shows an example for the mounting of the force receiving member on the cylinder cover.

FIG. 7, however, shows a preferred embodiment for the arrangement of the force receiving member 10 on the cylinder 6 and cover 8, respectively. The cover 8 is provided with a jacket 30, in which a ring 32, provided with an internal thread, is held between plate springs 33. The outer thread 35 of the rod 10 threads into the internal thread of the ring 32. The jacket 30 is closed by a cover 36, holding the plate springs 33 in the jacket. In this example, the adjustment of the rod 10 is made by rotation thereof as well. Preferably, the thread 35 and the inside thread of the ring 32 are provided with a coarse pitch. By the plate springs holding the ring 32 the strokes on the rod 10 are transmitted in dampened form on the cover 8 and the cylinder 6.

While there are shown and described present preferred embodiments of the invention, it is to be distinctly understood that the invention is not limited thereto, but may be otherwise variously embodied and practiced within the scope of the following claims.

I claim:

1. Pneumatic percussion tool comprising:
   a cylinder, a socket for a working tool,
a force receiving member, and
a piston arranged for displacement in said cylinder and acting as an oscillating striking member,
said piston being provided with a first surface, opposed to motion of said piston in a forward direction, to be acted upon by compressed air for propelling said piston in said forward direction towards said working tool, a second surface, opposed to motion of said piston in a backward direction, facing away from said first surface, to be acted upon by compressed air for propelling said piston in said backward direction, and with two striking surfaces, by which a stroke on said tool can be affected at both dead centers of said piston oscillations, each to generate a pulse advancing said working tool into a workpiece or retracting and loosening said working tool from said workpiece, respectively, said percussion tool comprising a single transfer port between said first and said second surface, said port being controlled by said piston, and at least one air outlet, said port and said outlet controlling the compressed air distribution for movement of the piston in said forward direction and in said backward direction, wherein the area of said first surface, the area of said second surface and the volumina of the cylinder volume defined by said cylinder and said first piston surface and the transfer port volume are selected such that at a predetermined piston position and a predetermined compressed air pressure value, the impact momentum of the forward moving piston is substantially equal to the impact momentum of the backward moving piston,
said force receiving member extending essentially coaxially to the longitudinal axis of said tool from a cylinder cover adjacent to said working tool into said cylinder, and being enclosed by within a piston hollow space defined by said piston, and said force receiving member having an impact surface at its end facing toward said working tool, said impact surface disposed to be acted upon at the piston dead center of the backward piston movement by a said striking surface provide inside said hollow piston space,
wherein said piston divides said cylinder into at least two cylinder volumes, which volumina depend on the position of said piston within said cylinder and a first cylinder volume is defined by said cylinder and said first piston surface having an area $A_1$, and a second cylinder volume is defined by said cylinder and said second piston having an area $A_2$, said transfer port is provided in the cylinder wall, connecting said volumina, said outlet is a piston controlled port connecting said first cylinder volume with the ambient pressure $P_0$ and a compressed air source with a pressure value $P_2$ feeding said second cylinder volume is provided, and wherein a first parameter A is defined as $$A = \frac{A_1}{A_2} \cdot \frac{P_0}{P_2} \text{ and}$$

$V_A$ is the volume of said first cylinder volume plus the volume of said transfer port, at the moment when the backward moving piston closes said outlet,
$V_{12}$ is the volume of said first cylinder volume plus the volume of said transfer port, at the moment when said backward moving piston opens said transfer port, and
$V_T$ is the volume of said first cylinder volume, plus the volume of said transfer port, at the dead center of the backward movement of said piston, and two parameters
$V_u$ and $V_o$ are defined as $$V_u = \frac{V_{12}}{V_A} \; ; \; V_o = \frac{V_T}{V_A} \text{ and}$$

the following conditions are met to attain equal impact momentums $$0.1 \leq A \leq 0.5$$

and $$0.1 \leq V_o \leq V_u \leq 0.8.$$

2. Pneumatic percussion tool according to claim 1, wherein said force receiving member is provided with a second impact surface, which is acted upon at the dead center of the forward piston movement by said second striking surface, which is formed by the inner surface of the piston head.

3. Pneumatic percussion tool according to claim 2, wherein said force receiving member is displaceably adjustable in the longitudinal cylinder axis, and wherein in a first adjustment position said second impact surface is acted upon by the piston at the dead center of the forward piston movement and said piston is braked by a compressed air cushion at the dead center of the backward piston movement, in a second adjustment position said first impact area is acted upon by said piston at the dead center of the backward piston movement and said piston is braked by a compressed air cushion at the dead center of the forward piston movement, and wherein in a third adjustment position none of said impact areas is acted upon by said piston and said piston is braked by a compressed air cushion at both of said piston's dead centers.

4. Pneumatic percussion tool according to claim 2, wherein said force receiving member is held in a support, said support being arranged displaceable and suspended by springs in said cylinder cover.

5. Pneumatic percussion tool according to one of claims 1 to 3, wherein said piston and said force receiving member are made of metal and said cylinder and said cover are made of one material of the group of light alloys, preferably aluminium, or plastics, preferably fiber reinforced plastics.

6. Pneumatic percussion tool according to claim 1, wherein said piston and said force receiving member are made of metal and said cylinder and said cover are made of one material of the group of light alloys, preferably aluminum, or plastics, preferably fiber reinforced plastics.

* * * * *

UNITED STATES PATENT AND TRADEMARK OFFICE
CERTIFICATE OF CORRECTION

PATENT NO.   : 5,152,352

DATED        : October 6, 1992

INVENTOR(S)  : Georges Mandanis

It is certified that error appears in the above-identified patent and that said Letters Patent is hereby corrected as shown below:

TITLE PAGE

Please include the following list of references under References Cited:

U.S. Patent Documents

```
4,121,499      10/24/78      Hay
4,651,833      03/24/87      Karpf et al.
5,057,112      10/15/91      Sherman et al.
```

Foreign Patent Documents

```
WO 89/06516    07/27/89      International
CH 661 239     07/15/73      Switzerland
DE 3148708     07/21/83      German
FR 2 339 751   01/28/77      French
```

Other Documents

EP Search Report, EP 90 12 2044, 07/18/92

Signed and Sealed this

Fourteenth Day of December, 1993

*Attest:*

BRUCE LEHMAN

*Attesting Officer*     *Commissioner of Patents and Trademarks*